(12) United States Patent
Kobayashi et al.

(10) Patent No.: US 7,132,289 B2
(45) Date of Patent: Nov. 7, 2006

(54) METHOD FOR INTRODUCING FOREIGN MATTERS INTO LIVING CELLS

(75) Inventors: Akio Kobayashi, Toyonaka (JP); Kiichi Fukui, Osaka (JP); Satoshi Harajima, Takatsuki (JP); Eiichiro Fukusaki, Suita (JP); Shinichiro Kajiyama, Takatsuki (JP); Shinya Okuda, Ibaraki (JP); Takeshi Shoji, Osaka (JP)

(73) Assignee: Osaka University, Osaka (JP)

( * ) Notice: Subject to any disclaimer, the term of this patent is extended or adjusted under 35 U.S.C. 154(b) by 690 days.

(21) Appl. No.: 10/015,607

(22) Filed: Dec. 17, 2001

(65) Prior Publication Data

US 2002/0115219 A1   Aug. 22, 2002

(30) Foreign Application Priority Data

Dec. 25, 2000  (JP) .............................. 2000-392167
Nov. 15, 2001  (JP) .............................. 2001-349559

(51) Int. Cl.
*C12N 15/09* (2006.01)
*C12N 5/10* (2006.01)
*C12N 15/63* (2006.01)
*C12N 15/88* (2006.01)
*A01H 5/00* (2006.01)

(52) U.S. Cl. .................... 435/460; 800/278; 800/288; 800/293; 435/470; 435/459; 435/458

(58) Field of Classification Search ................ 435/173, 435/293, 470, 458–460; 800/278, 288, 293
See application file for complete search history.

(56) References Cited

U.S. PATENT DOCUMENTS

| 4,945,050 A | 7/1990 | Sanford et al. |
| 5,013,660 A | 5/1991 | Kasuya et al. |
| 5,272,072 A | 12/1993 | Kaneko et al. |
| 5,916,788 A | 6/1999 | Kubota et al. |
| 6,346,101 B1 | 2/2002 | Alfano et al. |

FOREIGN PATENT DOCUMENTS

| EP | 0 137 504 A2 | 4/1985 |
| EP | 0 483 847 A2 | 5/1992 |
| EP | 483847 | * 6/1992 |
| JP | B2 62-7837 | 2/1987 |
| JP | B2-62-7838 | 2/1987 |
| JP | A 2-9378 | 1/1990 |
| JP | A-5-207827 | 8/1993 |
| JP | A 9-163984 | 6/1997 |

OTHER PUBLICATIONS

Gad, et. al. (Physiologia Plant. 1990, vol. 79, pp. 177-183.*
(Weber, et. al., Manipulation of Cells, Organelles, and Genomes by laser microbeam and optical traps, 1992, International Rev. of Cytology, vol. 133, pp. 1-41).*
Kurata et al., "The Laser Method for Efficient Introduction of Foreign DNA into Cultured Cells", Experimental Cell Research 162 (1986) pp. 372-378.
Buer et al., "Insertion of Microscopic Objects through Plant Cell Walls Using Laser Microsurgery", Biotechnology and Bioengineering, vol. 60, No. 3, Nov. 5, 1998.
Weber et al., "Manipulation of Cells, Organelles, and Genomes by Laser Microbeam and Optical Trap" International Review of Cytology, 1992, 133:1-41.
Tsukakoshi et al., "A novel method of DNA transfection by laser microbeam cell surgery", Applied Physics B, 1984, 35:135-40.
Palumbo et al., "Murine fibroblasts transfection by laser optoporation: preliminary notes on the use of a visible wavelength" Proceedings of SPIE-the International Society for Optical Engineering, 1994, 2328 (Biomedical Optoelectronic Devices and Systems II), 167-731.

* cited by examiner

*Primary Examiner*—David T. Fox
*Assistant Examiner*—Georgia Helmer
(74) *Attorney, Agent, or Firm*—Oliff & Berridge, PLC (57) ABSTRACT

A method for introducing a foreign matter into a cell, includes the steps of placing a small particle carrying a foreign matter at a part of a cell surface of a living cell, boring a hole in a cell wall and/or a cell membrane by irradiating and treating said part of the cell surface with a laser beam, and introducing the foreign matter into the living cell.

12 Claims, 6 Drawing Sheets
(6 of 6 Drawing Sheet(s) Filed in Color)

METHOD FOR INTRODUCING FOREIGN MATTERS INTO LIVING CELLS

BACKGROUND OF THE INVENTION

1. Field of the Invention

The present invention relates to a method for introducing a foreign matter into a living cell. Particularly, the invention relates to such a foreign matter into a living cell with use of a laser.

2. Related Art Statement

As the methods for introducing foreign matters such as genetic substances into living cells, there are known a method for directly introducing a foreign matter into a living cell with use of a fine glass tube (microinjection method), a method for applying a cell-fusing technique (a liposome fusion method and a protoplast fusion method), an introducing method using an infecting process (Agrobacterium method), a membrane permeability-promoting method (electropolation method), etc. when broadly classified.

According to the microinjection method, a fine micropipette is prepared with use of a glass tube, connecting it with a micromanipulator, and introducing a liquid of a foreign matter into a cell one by one under observation with a microscope. This method is a relatively excellent foreign matter-introducing method for animal cells having no cell walls.

As the cell fusion technique-applying methods, there are the liposome method, the protoplast fusion method, etc. According to the protoplast fusion method, a colon bacterium (*Escherichia coli*) or the like having a coloned plasmide is converted to a protoplast, which is fused with a target cell with ethylene glycol or the like, thereby introducing a gene into the cell. According to the liposome fusion method, a foreign matter is introduced into a target cell by using a liposome as a carrier.

As the infection process-utilizing introduction method, there is known a method for introducing a gene by using an Agrobacterium carrying a Ti plasmid.

According to the electropolation method based on the promotion of the membrane permeability, a cell is suspended in a solution of a foreign matter, and DC pulses at a high voltage upon the resultant solution or suspension, and thereby the foreign matter is introduced into the cell.

There is also known a gene gun method in which a fine metal particle coated with DNA is thrown into a cell of an organism, and thereby a gene is introduced into the cell through a cell wall and/or cell membrane. Furthermore, there is recently known a method for introducing a foreign matter into a cell by using a laser. These conventional methods for introducing the foreign matters into the cells are used mainly for transforming the target cells through the introduction of the foreign genes.

However, with recent progresses in the biotechnology, there have been the possibilities in diagnosis and treatment of diseases, molecular breeding of agricultural products imparted with various tolerances, production of useful products including livestock, etc. through introducing, into living cells, foreign matters other than genes, e.g., organella such as chloroplasts, nuclei, chromosomes and mitochondoria, physiologically active materials and indicators, functional proteins. Further, production of directly transformed bodies having undergone de-differentiation nor re-differentiation is conceivable in the case of plant, for example, by each introducing a foreign matter in a specified one cell of a living tissue. Thus, molecular breeding of many useful plants of which dedifferentiation or re-differentiation system has not been established are expected. Production of transformed products in which a plurality of characters are simultaneously transformed by simultaneously introducing plural kinds of foreign matters into a cell or cells is expected as well.

From this point of view, there are problems of difficulties in introducing foreign matters other than genes in the case of a gene-introducing method utilizing agrobacteria carrying Ti plasmides, a protoplast fusion method and a gene gun method among the conventional foreign matter-introducing methods. Further, a microinjection method, a liposome method and an electropolation method have a possibility of introducing foreign matters other than genes into cells, but the liposome method and the electropolation method require protoplast conversion when applied to plant cells, so that these methods have a problem in that there is difficulty in introducing a foreign matter into a specified one cell of a specific tissue. The microinjection method has a problem in that there is extremely difficult because skill is needed to handle a plant cell having a cell wall tougher than that of an animal cell. On the other hand, a laser method can introduce a foreign matter into a given target cell, but the conventional laser method has a problem in that there is difficulty in stably introducing foreign matters having extremely small physical strength, such as artificial chromosomes, or macrostructural bodies such as organella into cells.

Therefore, there have been strongly desires for development of a method which is easy to manipulate and has general-purpose applicability, which transforms a specified one cell as a target cell, and which can introduce a foreign matter such as not only genes but also foreign matters having extremely small physical strength, such as artificial chromosomes, or foreign matters such as macrostructural bodies such as organella into living cells irrespective of species of organisms. However, such a method for introducing the foreign matter into the living cell has not been known yet.

SUMMARY OF THE INVENTION

It is therefore an object of the present invention to provide a method in which a chemical bond of a bio-polymer constituting a cell wall is cut by utilizing a high processing characteristic of a laser beam, and thereby a foreign matter is introduced into a cell.

Having made investigations to solve the above-mentioned problems, the present inventors noted that tough cell walls, particularly plant cell walls, of living cells can be bored by utilizing the high processing characteristic possessed by the laser beam. Consequently, the inventors accomplished the present invention.

That is, the foreign matter-introducing method according to the present invention, comprising the steps of placing a small particle carrying a foreign matter at a cell surface of a living cell, boring a hole in a cell wall and/or a cell membrane by irradiating and treating said part of the cell surface with a laser beam, and introducing the foreign matter into the living cell.

In a preferred embodiment of the foreign matter-introducing method according to the present invention, the living cell is a cell of a plant, and at least a part of the cell wall of the plant cell is removed.

In a further preferred embodiment of the foreign matter-introducing method according to the present invention, at least part of the cell wall is removed by irradiation with a laser beam or by irradiation with the laser beam and treatment with a hydrolysis enzyme in combination.

In a still further preferred embodiment of the foreign matter-introducing method according to the present invention, the small particle is a fine particle having a particle diameter of 0.01 μm to 10 μm.

In a still further preferred embodiment of the foreign matter-introducing method according to the present invention, the small particle is a liposome including the foreign matter.

In a still further preferred embodiment of the foreign matter-introducing method according to the present invention, the small particle is a bead fixing the foreign matter.

In a still further preferred embodiment of the foreign matter-introducing method according to the present invention, the foreign matter is fixed by adding an aqueous solution containing at least the foreign matter and a curing agent into a water-in-oil type emulsion having a curable raw material in water, and forming a cured reaction product.

In a still further preferred embodiment of the foreign matter-introducing method according to the present invention, the curable raw material is sodium alginate, the curing agent is calcium chloride and the cured reaction product is calcium alginate.

In a still further preferred embodiment of the foreign matter-introducing method according to the present invention, the laser is at least one laser selected from the group consisting of a YAG laser, an exima laser, an Ar ion laser, a nitrogen laser and a nitrogen-excited color laser.

In a still further preferred embodiment of the foreign matter-introducing method according to the present invention, the foreign matter is at least one material selected from the group consisting of a genetic material, a protein material, an organella, a physiologically active material and an indicating agent.

In a still further preferred embodiment of the foreign matter-introducing method according to the present invention, the genetic material is at least one material selected from the group consisting of a DNA, a RNA, an oligonucleotide, a plasmid, a chromosome, an artificial chromosome, an organella DNA and a nucleic acid analogue.

In a second aspect of the foreign matter-producing method according to the present invention, a living cell is irradiated with a laser beam, a part of a cell membrane and/or a cell wall of the living cell is bored, and the foreign matter is introduced into the living cell from a laser beam-irradiated site with use of a microinjector. As the foreign matter, at least one material is selected from the group consisting of a genetic material, a protein material, an organella, a physiologically active material and an indicating agent. As the genetic material, at least one material is selected from the group consisting of a DNA, a RNA, an oligonucleotide, a plasmid, a chromosome, an artificial chromosome, an organella DNA and a nucleic acid analogue.

In a third aspect of the foreign matter-producing method according to the present invention, a living cell is irradiated with a laser beam, a part of a cell wall of the living cell is bored, a part of the cell membrane is exposed, a liposome including a foreign matter is placed on the exposed cell membrane, and the exposed cell membrane is fused with the liposome, and thereby the foreign matter is introduced into the living cell. As the foreign matter, at least one material is selected from the group consisting of a genetic material, a protein material, an organella, a physiologically active material and an indicating agent. As the genetic material, at least one material is selected from the group consisting of a DNA, a RNA, an oligonucleotide, a plasmid, a chromosome, an artificial chromosome, an organella DNA and a nucleic acid analogue.

A fourth aspect of the present invention is directed to a method for preparing a spheroplast or a protoplast, comprising the steps of irradiating one or plural cells in a living tissue of a plant with a laser beam, removing a part of a cell wall of the cell or cell walls of the cells, treating the living tissue of the plant with a hydrolysis enzyme, and selectively removing only a cell wall or cell walls around a laser beam-irradiated site of the plant living tissue.

In a preferred embodiment of the method for preparing a spheroplast or a protoplast, the living tissue of the plant is at least material one selected from the group consisting of a leaf, a root, a stem, a shoot apex, a root apex, an embryo cell, a seed, a pollen, a callus, a suspended cell, an adventive embryo and a nairy root.

A fifth aspect of the present invention is directed to a transformed body in which a genetic material is introduced into a living sell by using one of the foreign matter-introducing methods according to the present invention as mentioned above.

The foreign matter-introducing method according to the present invention irradiates the living cell with the laser beam, and utilizes the hole bored formed at a part of the cell wall and/or the cell membrane of this living cell. That is, the foreign matter-introducing method according to the present invention can be realized by using any one of (1) placing the small particle carrying the foreign matter around a bored hole, (2) introducing the foreign matter into the living cell by using the microinjector through a bored hole, and (3) placing the liposome including the foreign matter on around the bored hole and fusing the cell membrane with the liposome. As the living cells as targents of the present invention, animal cells, plant cells, microorganisms, etc. may be recited.

To begin with, the method (1) comprising the steps of placing a small particle carrying a foreign matter at a cell surface of a living cell, boring a hole in a cell wall and/or a cell membrane by irradiating and processing said part of the cell surface with a laser beam, and introducing the foreign matter into the living cell will be explained.

The laser to be used in the present invention is not particularly limited. The laser is excellent in that it has extremely excellent light-condensing ability, while giving almost no thermal influence upon a portion other than a laser beam spot. As the laser, the YAG laser, the exima laser, the Ar ion laser, the nitrogen laser, the nitrogen-excited color laser, etc. may be recited. The exima laser is preferred from the standpoint of view that a heat damage of the processed cell is particularly small, the processing accuracy is high, and the processed depth can be easily controlled by the irradiating energy and the number of times of irradiations.

The irradiating conditions of the laser upon the living cells can be appropriately changed depending upon the kinds of the living cells.

The diameter of the laser spot is in a range of 1 to 100 μm, for example. Preferably, it is in a range of 5 to 30 μm. The reason for that range is that it is a size large enough to introduce the foreign matter after the irradiation and that a damage upon the cell is small.

The energy density of the laser is not particularly limited, but is in a range of 1 to 100 mJ/cm$^2$. Preferably, it is in a range of 30 to 80 mj/cm$^2$. The reason for that range is that if it is less than 1 mj/cm$^2$, the cell wall cannot be sufficiently processed, whereas if it is more than 100 mj/cm$^2$, the laser penetrates the cell membrane and largely damages the cell.

Further, the laser may be applied in a range of the energy density higher than the above, particularly when the cell wall is to be completely removed with one irradiation. In this case, a preferred range of the energy density is 500 to 700 mj/cm$^2$. The reason why the energy density is set in that range when the cell wall is to be completely removed with one irradiation is that if it is less than 500 mj/cm$^2$, the laser cannot assuredly penetrate the cell wall, whereas if it is more than 700 mj/cm$^2$, the laser can penetrate but the living percentage of the cell decreases thereafter.

The output of the laser is preferably in a range of 1 to 1000 mj/cm$^2$, and more preferably 10 to 100 mj/cm$^2$.

The size of the hole bored through the irradiation with the laser beam is not limited, although depending upon the size of the foreign matter to be introduced. For example, the size of the bored hole is in a range of around 1 to 1000 μm$^2$. When a relatively large matter such as an organella is to be introduced, the size of the hole is in a range of around 100 to 1000 μm. When a relatively small matter such as a plasmid is to be introduced, the size of the hole is in a range of around 1 to 100 μm$^2$.

The laser beam is irradiated under the above conditions, thereby boring a hole in a part of the cell membrane and/or the cell wall of the living cell.

According to the present invention, the small particle carrying the foreign matter is placed at a part of the cell membrane. In the animal cell, the cell membrane is located at an outer periphery of the cell, and can be easily exposed. On the other hand, the cell membrane of the plant cell is located inside the cell wall, the cell wall needs to be removed. The cell wall can be removed by using an ordinary protoplast-converting method. Alternatively, all or a part of the cell wall can be removed by using the spheroplast-converting method or the protplast-converting method in the present invention as mentioned later. All or a part of the cell wall can be removed by irradiating it with the laser, while its irradiation degree is freely set and varied, so that a hole can be bored particularly locally in the cell wall. Consequently, while a number of sound cells are maintained in the vicinity of the irradiated cell, the foreign matter can be accurately introduced into only the desired cell, which can excellently transform and multiply only the specified cell into which the foreign matter is introduced.

As the small particle-placing method, a method using a micromanupulator, a pair of optical tweezers or the like can be recited, for example.

Now, how to prepare the small particle carrying the foreign matter will be explained. The small particle means a fine particle which can carry (include, adsorb, attach, etc.) the foreign matter and release the carried foreign matter after being introduced into the cell. As such fine particles, an alginic acid bead, a liposome, a metal particle such as a gold particle or a tungstein particle, a silicon carbide whisker, a mantle protein of a virus, etc. may be recited.

In the following, beads are explained as the small particles by way of example, but the invention is not intended to be limited thereto.

The material of the beads is not particularly limited, but a monovalent salt of alginic acid, an aqueous solution of κ-carrageenan or the like, and water-soluble gelled polysaccharides such as agar and gellan gum may be recited, for example.

The foreign matter can be carried on the small particle by adding an aqueous solution containing at least the foreign matter and a curing agent into a water-in-oil type emulsion having a curable raw material in water and forming a cured reaction product. As the curable raw material, sodium alginate may be recited, for example. As the curing agent, calcium chloride may be recited, for example. In this case, the cured reaction product is calcium alginate. In case a pair of optical tweezers are used to introduce the foreign matter into the cell with good operability, calcium alginate is advantageously used from the point of view that calcium alginate satisfies the following conditions (1) to (9) required for the optical tweezers method.

(1) The cured reaction product is a material which exists as a solution dissolving or suspending a foreign matter such as DNA before solidification, whereas after the solidification, it exists a solid or a gel stable to some extent in the aqueous solution.
(2) The cured reaction product passes light and has a refractive index higher than that of water so that manipulation may be possible with the optical tweezers.
(3) The cured reaction product has a specific gravity equal to or slightly higher than that of water.
(4) Manipulation steps are easy.
(5) The cured reaction product can be prepared by using ordinary materials and an ordinary device.
(6) The cured reaction product does not interrupt growth of the cell.
(7) After the bead preparation and the fixing, the foreign matter such as DNA is stably maintained in the cured reaction product.
(8) The cured reaction product can be processed to have a diameter of not more than 10 μm for introducing it into the cell.
(9) The cured reaction product releases the foreign matter inside the cell.

As the materials satisfying the above-mentioned conditions (1) to (9), liposomes, mantle proteins, etc. may be recited besides calcium alginate.

The above-mentioned water-in-oil type emulsion is obtained by an aqueous solution of a monovalent salt of alginic acid to a foreign matter introduced into a bead with an organic solvent not miscible with water and suspending the bead by an ultrasonic wave treatment. The resulting water-in-oil type emulsion is gelled by adding and mixing an aqueous solution containing cations of divalency or higher valency and the foreign matter into the emulsion. By so doing, the bead including the foreign matter inside and on the surface thereof can be formed in a particle diameter of 0.01 to 10 μm. The shape of the bead is not particularly limited, but preferably spherical.

The bead used in the present invention is preferably a bead of calcium alginate. The calcium alginate is used not only for the above-mentioned reasons, but also alginic acid is gelled with divalent calcium ions. The bead can be obtained by emulsifying a solution of alginic acid in an organic solvent/water emulsion system, then mixing calcium chloride with it and stirring them. The organic solvent used in emulsifying is not particularly limited, but isoamyl alcohol, butanol, etc. may be recited, for example.

The bead can be also prepared by converting the aluginic acid solution to a fine liquid drop by using a cell sorter and dropping it in the calcium chloride solution.

When a 0.5% to 3% aqueous solution of sodium alginate is added dropwise into an aqueous solution of about 50 mM calcium chloride, a gel which is semi-transparent and has a specific gravity higher than that of water can be prepared. Preferably, the concentration of the sodium alginate aqueous solution is 0.5% to 3%, and that of calcium chloride is 50 mM to 1000 mM. The reasons for these ranges is that if the concentration of the sodium alginate aqueous solution is not more than 0.25% or if the concentration of calciumchloride is not more than 25 mM, sodium alginate may not be gelled. Further, if the concentration of the sodium alginate is higher than 3%, the size of the liquid drop tends to increase on emulsifying. In order to prepare the bead having a practical size (10 μm to 0.1 μm), it is preferable that the concentration of the sodium alginate aqueous solution is 0.5% to 1.5%, and that of calcium chloride is 50 mM to 200 mM.

When the emulsion is suspended in an aqueous solution of 10 mM calcium chloride and the suspension is placed on a nylon mesh having a pore diameter of 5 μm, for example, and subjected to centrifugal filtration at 500 rpm for 5 minutes to remove beads having sizes of more than 5 μm, smaller beads can be prepared.

The beads are preferably stored in an aqueous solution of 10 mM calcium chloride. For, the sol formation is prevented, because the beads rapidly become a sol state in a solution containing EDTA or EGTA which chelates divalent cations or a solution containing monovalent cations at a high concentration.

The concentration of calcium is preferably less than 1 M. If it is more than 1 M, the beads are likely to be flocked, which may make it difficult to suspend again. If the centrifugal separation is effected at 7000 rpm or more for recovery, the beads are also likely to be flocked, which may make it difficult to suspend again.

As mentioned above, according to the present invention, the foreign matter can be introduced into the living cell via the small particle. As the foreign matter which can be introduced into the cell, at least one material selected from the group consisting of a genetic material, a protein material, an organella, a physiologically active material and an indicating agent may be recited.

As the genetic material, at least one material selected from the group consisting of a DNA, a RNA, an oligonucleotide, a plasmid, a chromosome, an artificial chromosome, an organella DNA and a nucleic acid analogue may be recited. As the protein, an enzyme, a functional protein, a hormon or the like may be recited. A the physiologically active material, a low molecular weight organic material, a polypeptide, an inorganic material, a saccharide, etc. may be recited.

The process in which the small particle carrying the foreign matter is taken into the living cell is explained as follows.

A hole can bored in a cell membrane in a given time period by irradiation with laser. The small particle can be flown into the cell through the hole thus bored. After the small particle is taken into the cell, the hole is closed, so that the cell membrane restores its original state. In fact, the hole is bored in the membrane in an instant by irradiation with the laser, and almost simultaneously the small particle flows into the cell.

If the small particle containing the foreign matter has an appropriate bead size, it can be taken into the cell of the plant through endocytosis.

The small particle thus taken into releases the foreign matter contained therein inside the plant cell. The size of the bead to be easily taken into is preferably 0.01 to 1 μm in particle diameter.

If the living cell is a cultured cell of an animal such as a human being or a Chinese hamster, the small particle is taken into the cell through phagocytosis, and releases the foreign matter, when the cultured cell of the plant is mixed with the bead. The size of the bead to be easily taken into is preferably 0.1 to 0.5 μm in particle diameter.

If the living cell is a yeast, the bead containing the foreign matter is taken into the yeast through endocytosis, when the small particle is mixed with the yeast converted in the form of a spheroplast. The size of the bead to be easily taken into is preferably 0.01 to 1 μm in particle diameter.

Next, explanation will be made on a case in which a hole is bored in a part of a cell membrane and/or a cell wall of a living cell by irradiating the living cell with a laser beam, and a foreign matter is introduced into the living cell with use of a microinjector through around the hole thus bored.

The same laser-irradiating conditions such as the kind, the irradiating condition, the spot diameter, etc. of the laser as in the cases of using the above-mentioned small particles can be applied in the method using the microinjector.

The same introducable foreign matters as those recited when the above-mentioned small particles are used can be used.

In the present invention, when the foreign matter is to be introduced into the living cell through around the bored hole, it may be introduced into the cell directly or via the above small particle containing the foreign matter.

When the foreign matter is to be introduced into the cell via the small particle, the same small particle-preparing method, the same conditions for the small particles, etc. as mentioned above can be employed. In case the small particle is to be introduced into the cell by the microinjection, it can be introduced while the foreign matter is included and thus protected in the small particle, if the foreign matter has small physical strength like an artificial chromosome, etc.

Next, explanation will be made on a method in which a hole is bored in a part of a cell membrane and/or a cell wall of a living cell by irradiating the living cell with a laser beam, a liposome including a foreign matter is placed on around the hole thus bored, and the foreign matter is introduced into the living cell.

The ordinary liposome method has poor efficiency, and needs complicated manipulation. However, according to the foreign matter-introducing method of the present invention, such defects can be overcome by boring the hole with the laser beam.

The liposome can be placed on around the hole by dropping a solution containing the liposome with use of a micro pipette, a glass capillary, a micromanipilator or the like. As the solution containing the liposome, a solution containing polyethylene glycol, mannitol, calcium chloride, etc. may be recited. Polyethylene glycol and calcium chloride are used to promote fusion between the liposome and the cell membrane. The concentration of each of them is appropriately adjusted depending upon the cell actually sampled. Mannitol is used to equalize the osmotic pressure between the exposed cell membrane of the cell and the solution to be dropped. The concentration of mannitol is also appropriately adjusted depending upon the cell actually sampled.

The combination of the laser and the liposome method has the following advantages. In the ordinary liposome method, it is necessary that the entire tissue sample of a target plant is treated with an enzyme, and a cell converted completely in the form of a protoplast is used, Therefore, a cell into which a foreign matter is to be introduced cannot be specified.

On the other hand, the combination of the laser and the liposome method according to the present invention, (1) target plants to which the invention method is applicable are selected over a wide range, because the entire plant tissue needs not be converted to a protoplast, and (2) a physically weak foreign matter can be assuredly led into the cell.

The same laser-irradiating conditions such as the kind, the irradiating condition, the spot diameter, etc. of the laser as in the cases of using the above-mentioned small particles can be applied in the invention method using the laser beam and the liposome method in combination.

The same introducable foreign matters as recited in the case of using the above-mentioned small particles can also be used.

Next, explanation will be made on a method in which a living tissue of a plant is converted to a spheroplast or a protoplast. in the spheroplast-or protoplast-converting method of the present invention, a part of a cell wall of a cell or a part of cell walls of plural cells is removed by irradiating the cell or cells with laser, and then a hydrolysis enzyme at a concentration lower than that employed in ordinarily converting the entire tissue to the protoplast is dropped on the living tissue of the plant.

As the living tissue of the plant, at least one kind selected from the group consisting of a leaf, a root, a stem, a shoot apex, a root apex, an embryo cell, a seed, a pollen, a callus, a suspended cell, an adventive embryo and a nairy root can be recited.

In the spheroplast-or protoplast-converting method of the present invention, At least a part of the living tissue of the plant, more specifically, only a part of one cell can be converted to the protoplast.

In general, the plant cell can very rarely be multiplied by planting only one cell in a medium different from a cell of a microorganism and that of an animal. For, The multiplication of the plant cell requires the presence of a number of sound cells adjacent around it. These sound cells are generally called nurse cells. That is, in order to start the multiplication, one cell needs to be supplied with nutrition, a growth-requisite hormone or the like from other cells adjacent thereto.

Therefore, it is presumed that even if a foreign matter is introduced into a cell obtained by the ordinary protoplast-preparing method, it is difficult to multiply the foreign matter-introduced cell.

However, when the invention method is used, only a part of one cell can be converted to a protoplast, and at the same time the cells around the one partially converted to the protoplast can be kept sound. Therefore, according to the present invention, the protoplast-converted cell can be mutiplied at a high probability even after the foreign matter is introduced into it. Particularly in case the foreign matter is a genetic material, it is expected that the transformation-realizing efficiency can be raised.

As the cell wall-decomposing enzyme, cellulase, pectolyase, macerozyme, dorisynthesis, etc. can be recited, for example. The concentration of the cell wall-decomposing enzyme is not particularly limited depending upon the kind, the size, the growing time period, etc. of the plant cell to be treated, but it may be set to a range of 0.1% to 2%, which is lower than the enzyme concentration ordinarily used for ordinary protoplast conversion. By so doing, only the vicinity of the cell processed with the laser can be converted to the protoplast.

The same laser-irradiating conditions such as the kind, the irradiating condition, the spot diameter, etc. of the laser as in the cases of using the above-mentioned small particles can be applied in the spheroplast-or protoplast-converting method according to the present invention.

As to the transformed body according to the present invention, a genetic material is introduced by using the above-mentioned foreign genetic material-introducing method.

As mentioned above, according to the foreign matter-introducing method of the present invention, it is possible to introduce the organella such as a nucleus or a chromosome of the same or different organism or a huge DNA such as a artificially prepared chromosome into a living cell. Therefore, multigene, which has been difficult to introduce, can be introduced together. For example, a group of genes participating in biosynthesis of a useful physiologically active substance can be introduced together to effectively produce such a substance in a living thin growing fast.

Further, as mentioned above, the foreign matter-introducing method according to the present invention can introduce a plant hormone into a plant. Therefore, when one wishes to control the growth of a tissue near an introducing site, the growth of a specified site of a specified plant can be controlled by introducing into an intended plant cell an auxin such as indoleacetic acid and naphthaleacetic acid, a cytokinin such as zeatin and kinetin, absccisic acid, gibberellin or peptide-based hormone according to the foreign matter-introducing method of the present invention.

When a antibacterial substance such as phytoalexin, more specifically, pisatin, phaseolin, medicarpin, rishitin or rishitinol is introduced likewise, disease tolerance of a tissue likely to be infected with pathogenic bacteria can be improved or completely sterilized cells free from viruses and bacteria can be prepared. In addition, tolerance against stress such as UV or light in a light-receiving tissue of a leaf or the like and that against stress such as a heavy metal in a root portion can be improved by incorporating an active oxygen such as phytochelatin or glutathione.

BRIEF DESCRIPTION OF THE DRAWINGS

The file of this patent contains at least one drawing executed in color. Copies of this patent with color drawings will be provided by the Patent and Trademark Office upon request and payment of the necessary fee.

For a better understanding of the invention, reference is made to the attached drawings, wherein:

FIG. 2(a) is a fluorescent image obtained by observing the fluorescent light, and FIG. 2(b) a bright-field mage.

FIGS. 4(a) and 4(b) are bright-field images of the epidemic of the onion observed.

The application file for this application contains at least one drawing and/or photograph executed in color. Copies of this patent application publication with color drawings and photographs will be provided by the Office upon request and payment of the necessary fee.

In the following, the present invention will be explained more concretely based on the following examples, but the invention should not be interpreted to be limited to them.

EXAMPLE 1

A substance was tried to be introduced into a cell at the time of irradiation with a laser. calcein, which is a calcium ion indicator and often used for confirming the introduction of substances into cells, was employed as the material to be introduced. A 0.1~1μ drop of the substance to be introduced (a solution of calcein) was dropped on an epidermic cell of an onion. A hole of 10×10~30×30 μm was bored in the onion epidermic cell through the dropped solution with an exima laser at an energy density of 30 to 90 mJ/cm$^2$. It was confirmed with a fluorescent microscope that calcein was introduced into the cell simultaneously with the formation of the hole in the onion epidermic cell by the laser. Further, it was confirmed with an MTT that the cell processed with the laser lived 24 hours after it was processed.

Figure 1:
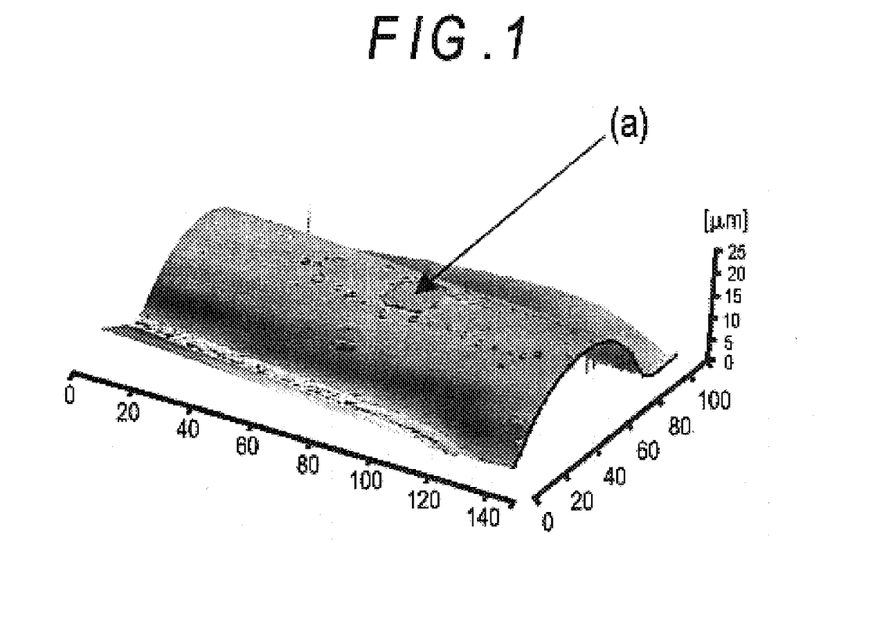
FIG. 1 is an image of the cell wall part of which was removed by laser irradiation.

The state of a cell wall of which was partially removed by the irradiation with the exima laser was three-dimensionally analyzed with a color laser 3D profile microscopy. The cell wall was obtained from the onion epidermic cell, and the laser-applying conditions were an energy density of 60 mJ/cm$^2$, an irradiation area of 20×20 μm$^2$ and a wavelength of 193 nm. Results are shown in FIG. 1. FIG. 1 shows the shape of a pore of the cell wall of the onionepidermiccell treated with the laser beam. It can be clearly confirmed from FIG. 1 that the pore was formed by processing with the laser, while the cell swelled (FIG. 1(a)).

Next, a foreign matter was tried to be introduced into a living cell by actually using a small particle. As the foreign matter, FLUORESCEIN ISOTHIOCYANETE-D EXTRAN (common name: FITC-Dextran) commercially available from Sigma Co., Ltd. was used. There was no limitation on the molecular weight of the FITC-Dextran.

Preparation of Small Particles

Into a 1.5 micro-centrifugal tube were separately introduced 1% sodium alginate (100 μl) and isoamyl alcohol (900μ). The mixture was subjected to sonication for 15 seconds. Into the solution was added a 100 mM solution of calcium chloride containing dexitran labeled with FITC, thereby suspending small particles. The small particles were passed through a nylon mesh (pore size 10 μm) by centrifugal operation at 2000 rpm for 5 minutes. The resulting particles were passed through a mesh having a pore size of 5 vm again by centrifugal operation, thereby obtaining small particles. These small particles were used to be introduced into cells.

Introduction of a Small Particle into a Cell

Aepidermiccell was cut out from an onion grown by a hydroponic method in two days, and placed on an MS solid culture. A part of a wall cell was removed by irradiating an introduction-targeted cell with an ArF exima laser beam (193 nm) in an irradiation area of 100 μm$^2$ at an energy density of 40 mJ/cm$^2$. On this site was dropped, with a micromanipulator, about 0.1 μl of an aqueous solution in which FITC dextran-including small particles prepared above were suspended. Then, an ArF eximer laser beam (193 nm) was irradiated upon the site through the dropped solution in an irradiation area of 100 μm$^2$ at an energy density of 10 mJ/cm$^2$, thereby introducing a small particle into the cell.

Figure 2:
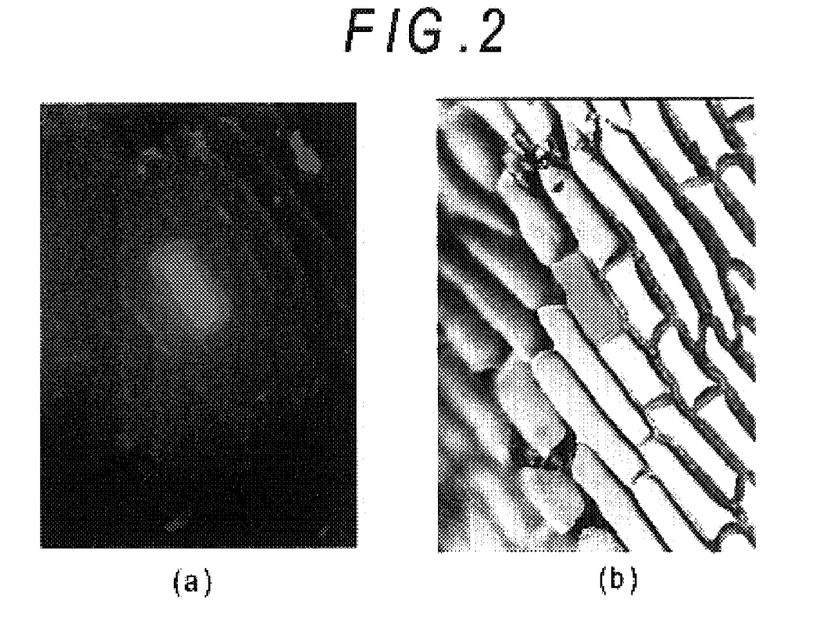

The small particle introduced was conformed in the following manner. The introduction of the small particle into the cell was confirmed by observing a fluorescent light of the FITC under a colarant-separating IB excited (U-MNIBA) filter with use of a fluorescent microscope in which an erected microscope of OLYMPUS BX 50 type was attached with an incident-light fluorescent device BX-FLA. FIG. 2(a) shows a fluorescent image obtained by observing the fluorescence light, and FIG. 2(b) does a bright-field image. As a result, living cell were sound with no abnormality observed.

EXAMPLE 2

Next, a foreign matter was tried to be introduced into a cell by using the microinjection method after laser irradiation.

A hole, 10×10~30×30 μm, was bored in aepidermiccell of an onion with the exima laser at an energy density of 30~90 mJ/cm$^2$. A calcein solution was introduced into the cell by using the microinjection through the hole bored in the laser processing. It was observed with the fluorescent microscope that the calcein solution was introduced into the cell.

EXAMPLE 3

Thirty days after a seed of a tobacco SR-1 plant was planted in a MS medium, a cotyledons was used and laser processed with an exima laser. The energy density of the laser was 30 to 90 mJ/cm$^2$, and a hole was bored in a size of 10×10~30×30 μm. A cell wall-digesting enzyme was dropped to the hole bored by the laser processing. Twenty four hours later, a protoplast cell of a mesophyll in which a cell wall near the hole was digested was isolated and observed.

EXAMPLE 4

Introduction of Liposome into a Cell
FITC-DEXTRAN
FLUORESCEIN ISOTHIOCYANETE-DEXTRAN (common name: FITC-DEXTRAN) commercially available from Sigma, Co., Ltd. was used. There was no limitation on the molecular weight of the FITC-DEXTRAN used.

Preparation of Liposome

Each of L-α-Dioleoyl Phosphatidyl ethanolamine and N-[1-(2,3-Dioleoyloxy)propyl]-N, N, N-trimethyl-ammonium was dissolved in chloroform at a concentration of 5 mg/ml. The resulting solutions were mixed at 200 μl:200 μl, and the chloroform was completely evaporated from the mixed solution at a low temperature under reduced pressure. A thin film of lipid was formed simultaneously with the evaporation. To this thin film was added 50 μl of a sample solution containing FITC-Dextran, which was left still on the film for 5 minutes. Then, 450 μl of a buffer solution: 10 mM Tris-HCl, pH 5.8 was added thereto, and left still for 15 minutes. The thin film of the lipid, the sample solution and the buffer solution were mixed under stirring with a vortex, thereby preparing a liposome including FITC-Dextran.

Introduction of the Liposome into a Cell

An epidermic cell was cut out from an onion grown by hydroponic method for 2 days, and imbedded in a MS solid medium. An exima laser beam was irradiated upon the onion epidermic to process the epidermic. At that time, the irradiating area was 100 to 400 μm$^2$, and the energy density was 20 to 60 mJ/cm$^2$. An aqueous suspension (6% polyethylene glycol and 0.1 M mannitol contained) of the liposome including the FITC dextran as prepared above was dropped on the processed epidermic. An exima laser beam was irradiated upon the dropped aqueous suspension.

Observation of Liposome Introduced

While the fluorescent light of the FITC was observed under a colorant-separating IB excited (U-MNIBA) filter with use of a fluorescent microscope in which a erected microscope of OLYMPUS BX 50 type was attached with a vertical fluorescent device BX-FLA, and a small particle was introduced into a cell.

EXAMPLE 5

Next, a genetic material was tried to be introduced into a cell. More specifically, a genetic material absorbed on a gold particle or a magnetic particle was tried to be introduced.

First, 60 mg of gold particles were measured in a 1.5 ml fine amount-centrifugal tube. Into the particles was added 1 ml of a 70% solution of ethanol, followed by 5 minute stirring. After the resultant was left still for 15 minutes, it was subjected to centrifugal separation at 10000 rpm for around 3 to 5 seconds (Centrifugal device HITACHI himac CF15R centrifugal separator, T15A23 rotor). After a supernatant liquid was removed, the remainder was stirred for 1 minute after 1 ml of sterilized water was added. After the mixture was left still for one minute, centrifugal separation was effected at 10000rpm for around 3 to 5 seconds. The above procedure was repeated twice. Then, a supernatant liquid was removed, a remainder was suspended in 1 ml of a 50% solution of glycerol added. Into fine amount centrifugal tubes were separately introduced 1.5 ml fine amounts of the suspension, which were stored at −20° C. until use. Then, 25 µl of the gold particles introduced into the centrifugal tube and stored at −20° C. was led into a fresh 1.5 ml fine amount centrifugal tube, which was stirred well. Into the tube was 3 µg of plasmide DNA (concentration 1 mg/ml), followed by stirring for 2 to 3 minutes. Then, 25 µl of 2.5 M $CaCl_2$ was further added to the resultant, followed by stirring for 2 to 3 minutes. Thereafter, 10 µl of 0.1 M spermidine was further added to the resultant, followed by stirring for 2 to 3 minutes. After the mixture was left still for 1 minute, it was subjected to centrifugal separation at 15000 rpm for 1 second. After a supernatant liquid was removed and 70% ethanol was added to the remainder, the mixture was flown along the wall of the tube. Then, a supernatant liquid was removed. The above procedure was repeated with 100% ethanol. Finally, the product was suspended in 30 µl of 100 ethanol, and a necessary amount of the suspension was filled in a capillary for use. With respect to magnetic particles, the same procedures were effected. The god particles having a particle diameter of 1 µm were used. The magnetic particles having a diameter of 20 nm were used. The plasmid DNA was purified by using Quantum Prep manufactured by BIO-RAD Co., Ltd.

The plasmid DNA absorbed with the gold particles were used for the introduction.

An edipermic cell of an onion was implanted in a 0.5% agar medium containing 0.5 M mannitol, which was subjected to plasma separation. A cell wall was completely removed by processing a gap (space), which was formed between the cell wall and a cell membrane by the plasma separation, with laser in a square area of 10 µm×10 µm at a laser energy density of 600 $mJ/cm^2$. A foreign matter was introduced into the inner gap through a laser-formed pore by microinjection. The foreign matters used were the gold particles and magnetic particles absorbing the plasmid DNA, plasmid DNA-including alginic acid beads, liposome, etc. After the introduction of the foreign matter, the onion epidermic was implanted in a 0.5% agar medium containing 0.2 M mannitol to recover a plasma. Then, after 24 hour culture, expression of the gene used for the introduction was observed.

More specifically, as the genetic information material used for the foreign matter, a chimera gene in which a gene (Green Fluprescense Protein (GFP)) encoding a fluorescent green light emission protein of the jellyfish (*Aequorea victoria*) is connected to a downstream of a 35S promoter of a cauliflower mosaic virus was used. This chimera gene is introduced into a plant cell, and expressed to produce a protein which emits a green fluorescence. Judgment was made based on whether the expression was effected or not through observing the light emission by using plasmid DNA including this chimera gene. The luminescent light was observed with the erected fluorescent microscope (BX-50) manufactured by Olympus Co., Ltd. (BX-50). More specifically, a bright-field image and a fluorescent image were observed with this microscope. A fluorescent filter used in this fluorescent observation was a U-MWIB2, U-MWIBA2 or U-MNIBA2.

EXAMPLE 6

DNA plasmid absorbed on gold particles or the like were tried to be introduced in the same manner as in Example 5.

An epidermic cell of an onion was implanted in a 0.5% agar medium containing 0.5 M mannitol, which was subjected to plasma separation. A cell wall was partially or completely removed by processing a gap (space), which was formed between the cell wall and a cell membrane by the plasma separation, with laser in a square area of 10 µm×10 µm at a laser energy density of 600 $mJ/cm^2$. A solution containing a foreign matter such as the gold particles or magnetic particles absorbing the plasmid DNA, plasmid DNA-including alginic acid beads or liposome or the like was dropped on the pore formed by the laser processing according to the microinjection. Then, laser irradiation was effected again, so that the foreign matter-containing solution was flown into the gap (space) formed by the separation of the plasma. The onion epidermic cell was implanted in a 0.5% agar medium containing 0.2 M mannitol to recover a plasma. Then, after 24 hour culture, expression of the gene used for the introduction was observed with the fluorescence microscope. The observation was effected by using the gene encoding the fluorescent green light emission protein of the jellyfish (*Aequorea victoria*) in the same manner as in Example 5.

EXAMPLE 7

Next, while laser processing was being effected, introduction was tried again for a cell preliminarily processed with laser.

As a material to be introduced, DNA plasmid absorbed on gold particles in the same manner as in Example 5 was used.

A part of a cell wall was peeled off by laser processing a epidermic cell of an onion in a square area of 10 µm×10 µm at a laser energy of 60 $mJ/cm^2$. A solution containing gold particles or magnetic particles absorbing the plasmid DNA was dropped on the pore formed by the laser processing according to the microinjection. The foreign matter was introduced into the cell by effecting laser irradiation again. After the foreign matter was introduced, the laser treated cell was cultured for 24 hours, and expression of the gene was observed with the fluorescent microscope.

The observation was effected by the using gene encoding the fluorescent green light emission protein of the jellyfish (*Aequorea victoria*) in the same manner as in Example 5.

Figure 3A:
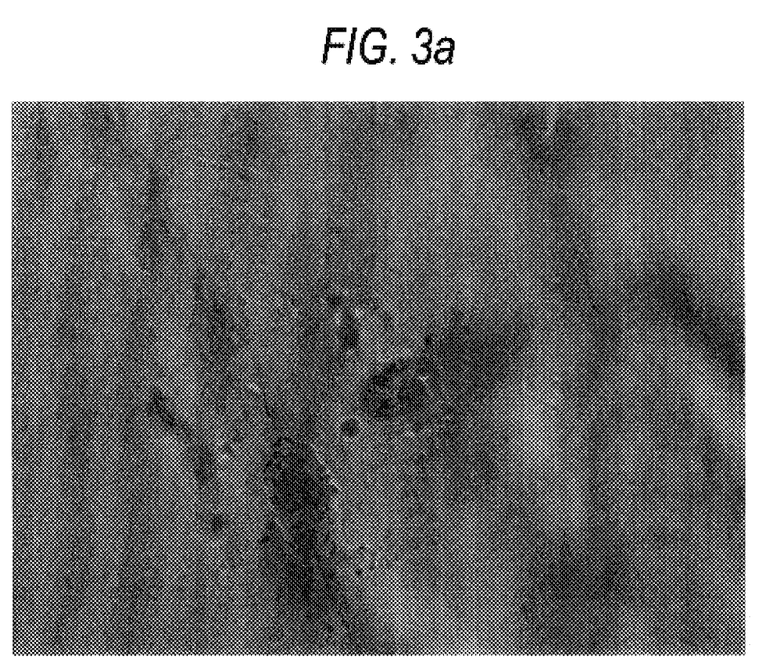
FIGS. 3(a) and 3(b) are photographs showing that gold particles are introduced into a cell by laser irradiation, FIG. 3(a) being a microphotograph obtained by focusing the surface of the cell, and FIG. 3(b) a microphotograph in which an interior of the cell is focused.
Figure 3B:
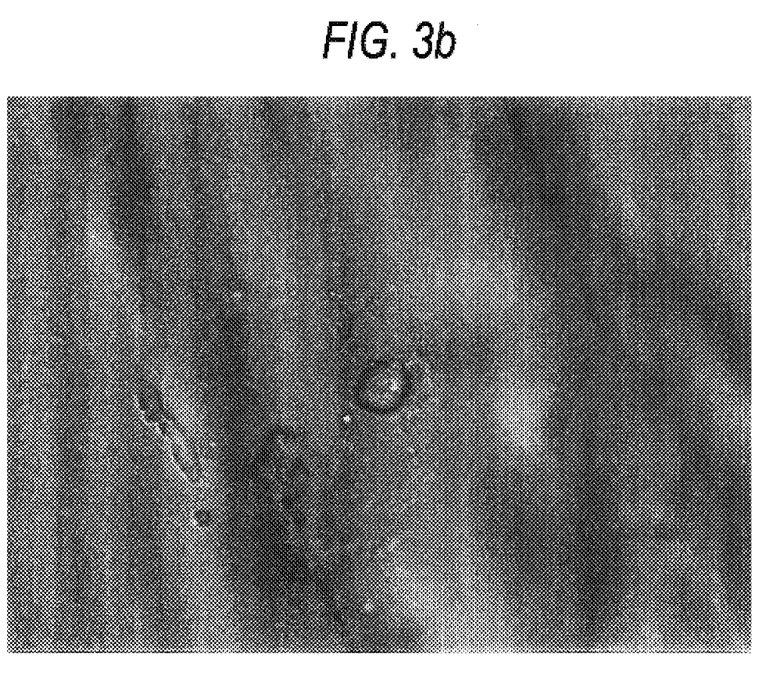

FIGS. 3(a) and 3(b) are photographs showing that gold particles are introduced into a cell by laser irradiation. FIG. 3(a) is a microphotograph obtained by focusing the surface of the cell. This microphotograph is a bright-field observed image obtained when a surface layer of the epidermic cell of the onion was peeled off by the laser processing, and the gold particles were placed on the pore processed portion by the micromanipulator. In this picture, the surface of the cell was focused. FIG. 3(b) is a microphotograph in which an interior of the cell is focused. With respect to the above sample, focusing was shifted to the interior of the cell. This reveals that the gold particles exist inside the cell.

EXAMPLE 8

Next, complete removal of a part of a cell wall and introduction of a material were tried to be effected by laser processing a plant cell and using a cell wall-decomposing enzyme in combination.

Exima laser was irradiated upon a epidermic cell of a stem of a torenia plant. The laser irradiation was effected in a square area (size) of 5×5~10×10 μm. At that time, the energy density was 60 to 80 μJ/cm$^2$. After the laser processing, the cell wall-decomposing enzyme (0.1% Pectolyase Y23, 1% cellulase Onozuka R S, 0.4M Mannitol, pH 5.5) was directly dropped on the laser-processed site by using a microcapillary. Thereafter (around 15 minutes to 30 minutes later), the cell was washed with sterilized distilled water (Decomposition of the cell was terminated by washing off the enzyme solution). It was confirmed with the erected microscope that the cell wall near the laser-processing site was decomposed and depressed. In order to confirm that the cell wall was completely removed, a 0.1% aqueous solution of Fluostain was directly dropped on the laser-processed site by using a microcapillary. After dying for 5 minutes, that site was observed with the fluorescent microscope, which confirmed that the laser-processed portion was not dyed. On the other hand, when a cell was merely processed with laser at a weak energy density and subjected to the same treatment as above, it was observed that the laser-processed site was dyed. Therefore, it is considered that the cell was completely removed through decomposition when the liquid containing the cell wall-decomposing enzyme was applied to the laser-processed site.

Next, a microcapillary was pierced into the above processed site by the microinjection to introduce a DNA solution. In the DNA solution, a plasmid DNA having GFP was employed. After the microinjection, a plant was transferred to a MS plate medium, followed by culturing for 24 hours. Fluorescence of GFP was observed by using the fluorescent microscope (Olympus BX50).

Figure 4A:
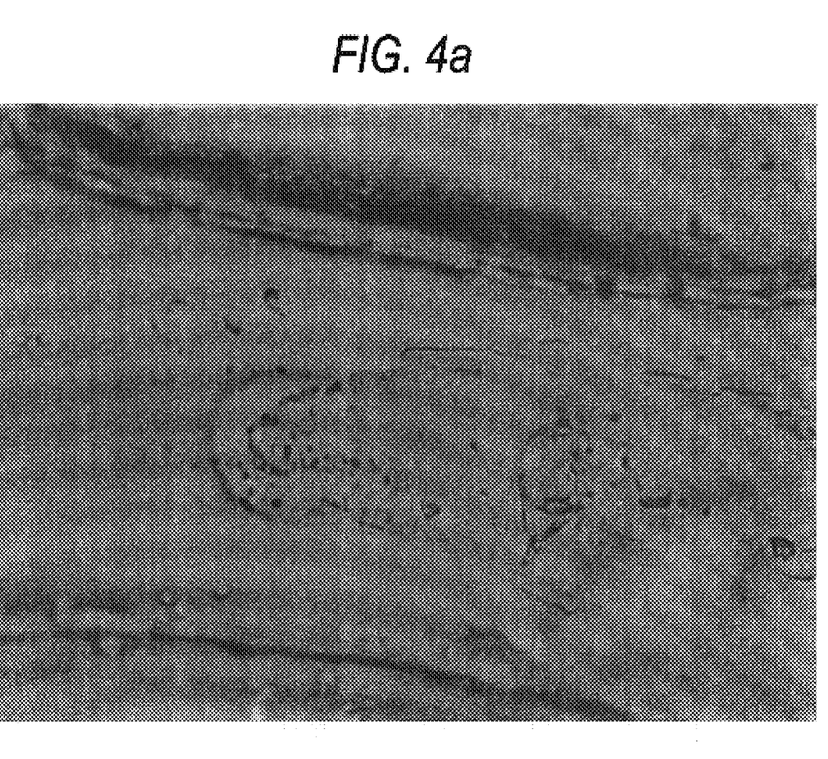
FIG. 4(a) gives a bright-field image of the laser-processed onion epidermic cell at a left side and that of the cell laser-processed and then treated with the enzyme at a right side, FIG. 4(b) giving a bright-field image of the above observed with a incident-light source.
Figure 4B:
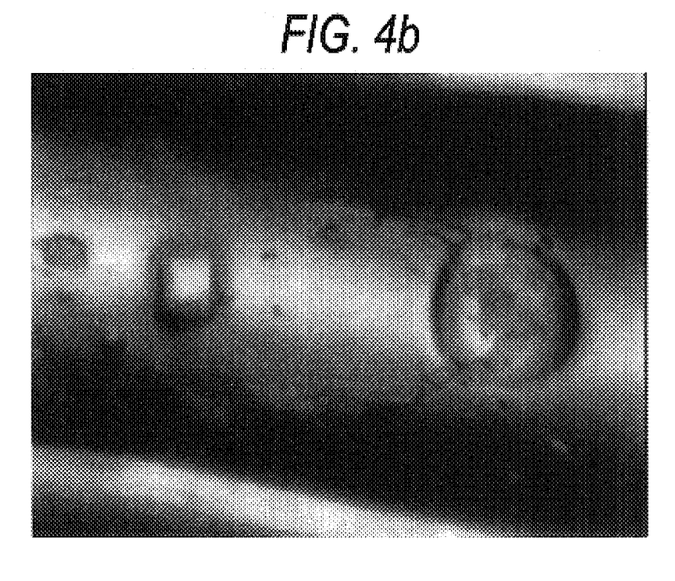

FIGS. 4(a) and 4(b) are bright-field images of the epidermic cell of the onion observed. FIG. 4(a) gives a bright-field image of the laser-processed onion epidermic cell at a left side and that of the cell laser-processed and then treated with the enzyme at a right side. FIG. 4(b) gives bright-field images of the above observed with the incident-light source.

Figure 5:
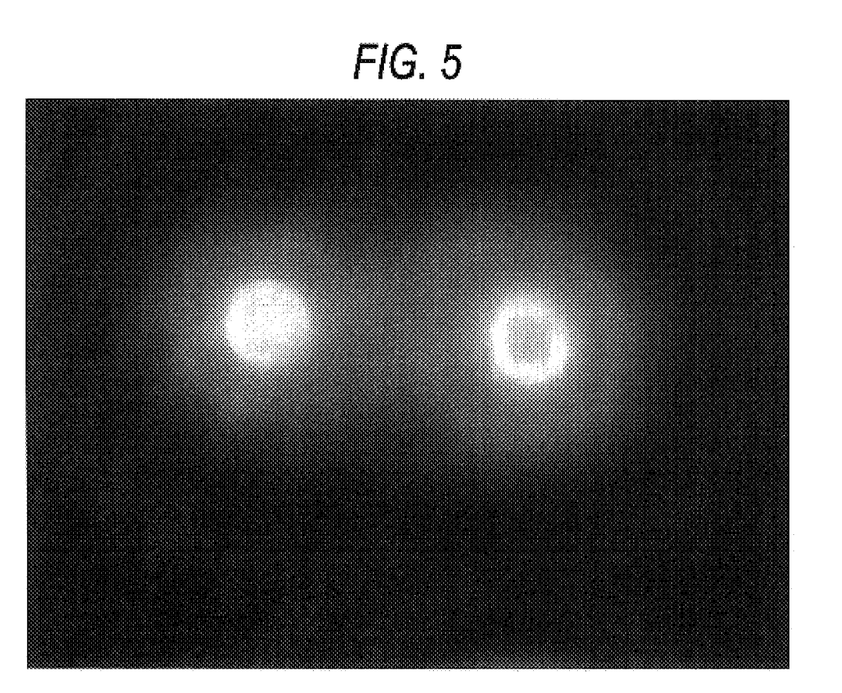
FIG. 5 is an image obtained with a fluorescent light through observation of the above sample dyed with a cell wall-dying reagent, Fluostain, by using the fluorescent microscope.

FIG. 5 is an image obtained with a fluorescent light through observation of the above sample dyed with a cell wall-dying reagent, Fluostain, by using the fluorescent microscope. In the right image, a center portion is not dyed with the reagent as seen by comparison with the left side image. Thus, it is considered that a cell membrane is exposed in the right image.

Figure 6:
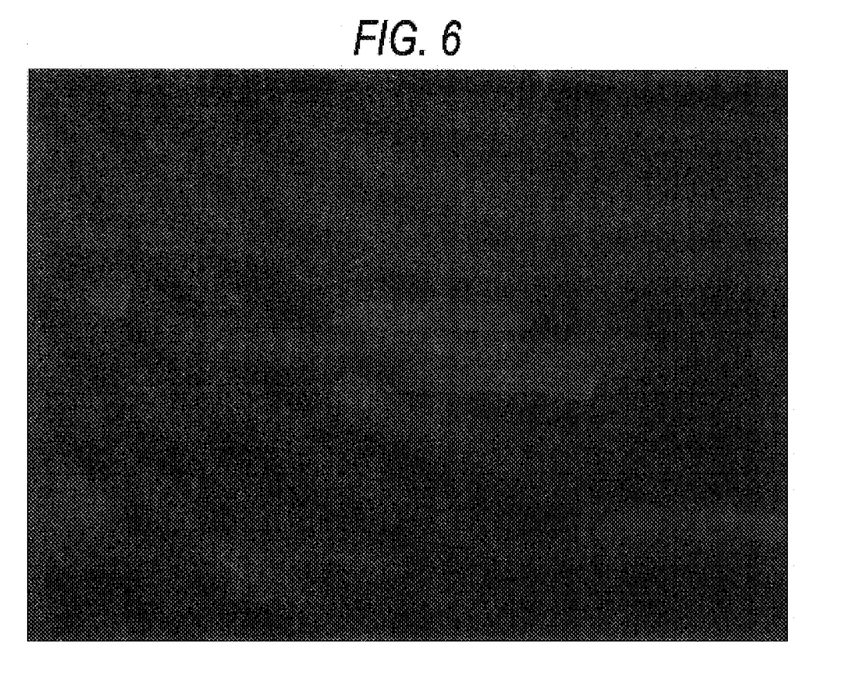
FIG. 6 shows a transient expression of sGFP.

FIG. 6 shows a transient expression of sGFP. That is, FIG. 6 is an image obtained by observing expression of sGFP with the fluorescent microscope after laser was irradiated upon the epidermic cell of a stem of a torenia plant, the cell was treated with the enzyme and then the sGFP plasmid solution was introduced by the microinjection method, and the cell was cultured for 24 hours. As is clear from this image, the fluorescent protein was expressed by the gene introduced.

In this Example, the microcapillary was used in the enzyme treatment, but needless to say such can be effected without use of the microcapillary. For example, the laser-processed face is immersed in the enzyme solution, and reacted with it for a few or several minutes, and washed with sterilized distilled water so as to perform the enzyme treatment.

EXAMPLE 9

A plasmid solution (containing sGFP) was introduced by using the same method as in the case of introducing the calcein solution as described in Example 2, and expression of the sGFP was confirmed with the fluorescent microscope after 24 hour culturing.

Figure 7:
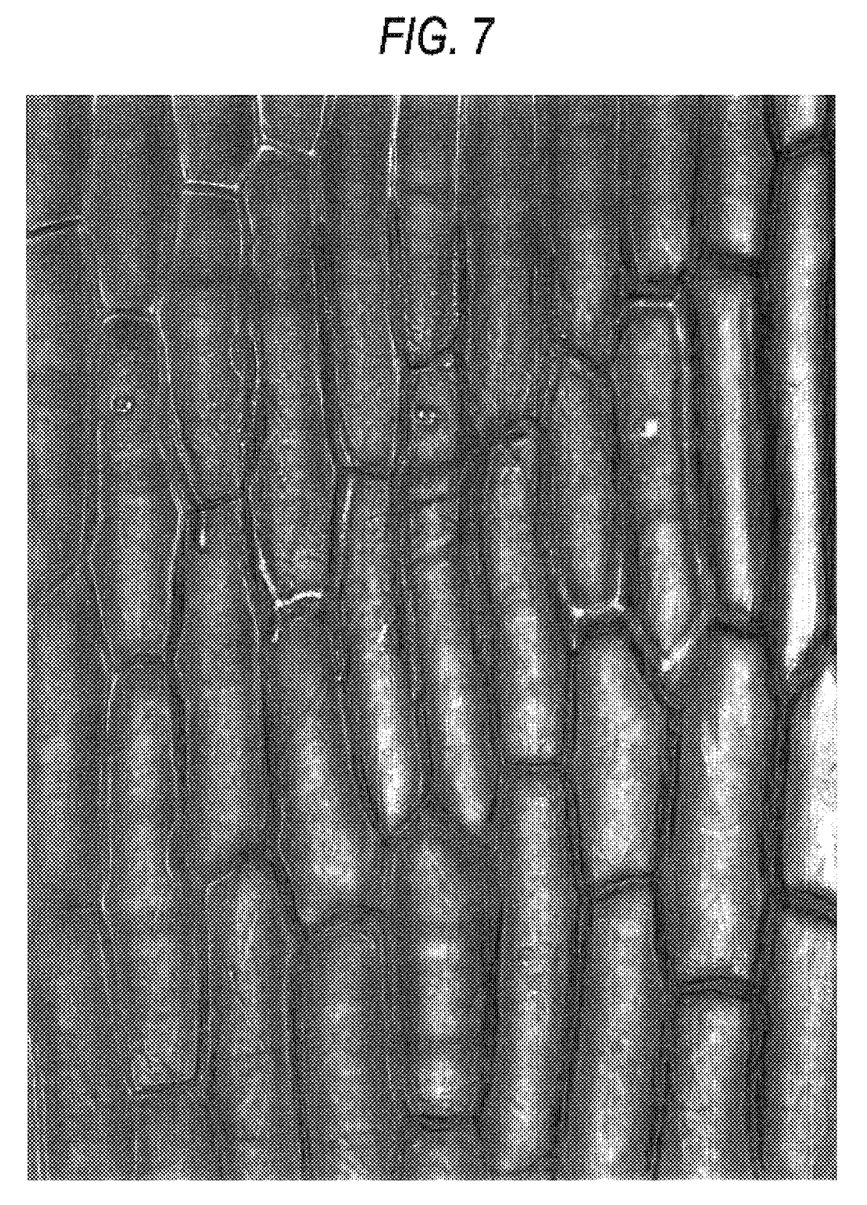
FIG. 7 is a bright-field image of an epidermic cell of an onion observed.
Figure 8:
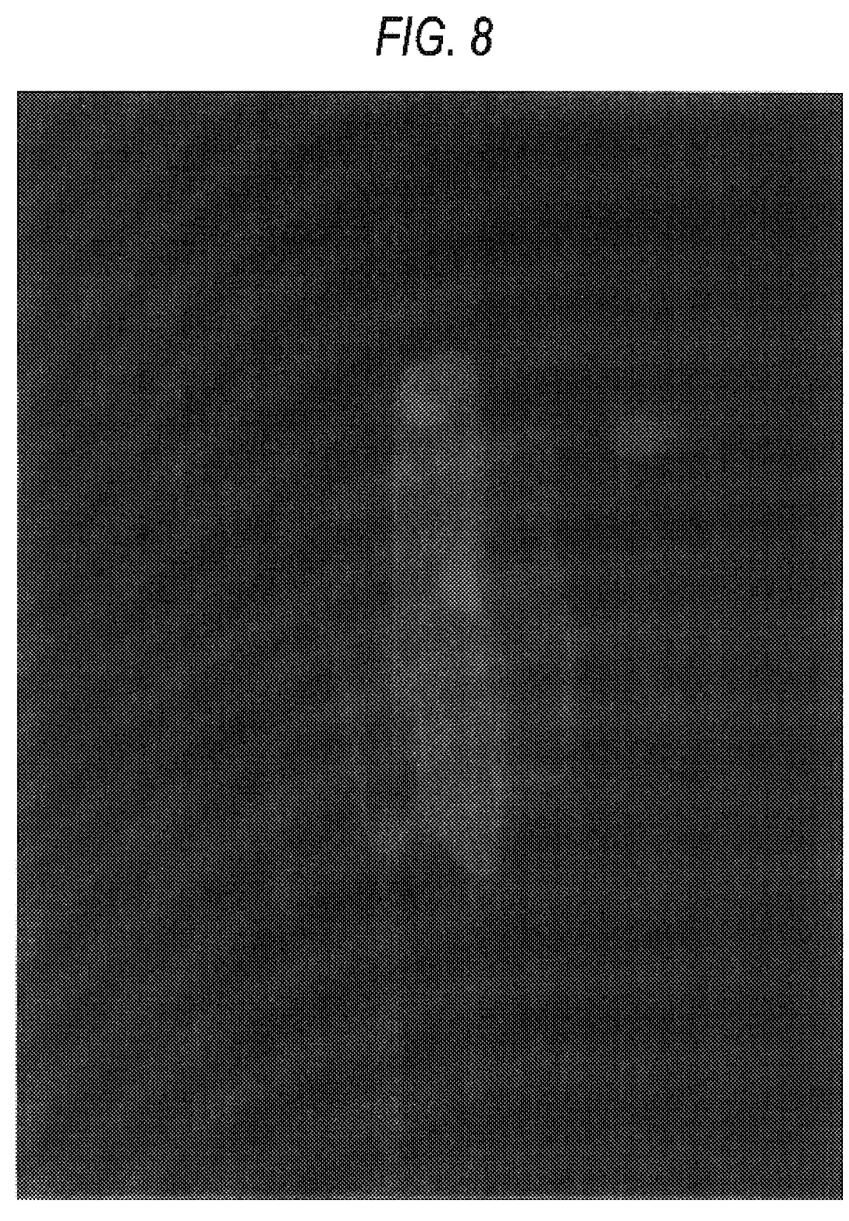
FIG. 8 is a microphotograph showing that the sGFP plasmid solution was introduced into a cell and transiently expressed there.

FIG. 7 is a bright-field image of epidermic cell of an onion observed. That is, FIG. 7 gives the bright-field image of epidermic cell of the onion observed after 24-hours cultivation following the laser processing and the injection of the plasmide solution. FIG. 8 is a microphotograph showing that the sGFP plasmid solution was introduced into a cell and transiently expressed there. FIG. 8 is to see the expression of the sGFP through observation of the sGFP-containing plasmid in FIG. 7 with the fluorescent microscope.

The foreign matter-introducing method of the present invention exhibits an advantageous effect that a single specified cell can be used as a target cell in producing a transformed plant by introducing the foreign matter or the gene therein.

The foreign matter-introducing method of the present invention exhibits another advantageous effect that the target plant species to be irradiated with laser is not limited different from cases where plant pathogenic bacteria are used, and therefore the method is used for general purposes.

The foreign matter-introducing method of the present invention exhibits a further advantage that a large-size foreign matter such as a nucleus or a chromosome can be introduced into a cell.

The matter-introducing method of the present invention exhibits a still further advantage that plural kinds of foreign matters can be simultaneously introduced into a cell.

The matter-introducing method of the present invention exhibits a still further advantage that a foreign matter having a low physical strength can be stably introduced into a cell.

What is claimed is:

1. A method for introducing a foreign matter into a cell, comprising the steps of:
   placing a small particle carrying a foreign matter at a part of a cell surface of a living cell wherein the small particle is a bead fixing the foreign matter,
   boring a hole in a cell wall and/or a cell membrane by irradiating and treating said part of the cell surface with a laser beam, and
   introducing the foreign matter into the living cell.

2. The method set forth in claim 1, wherein the living cell is a cell of a plant, and at least a part of the cell wall of the plant cell is removed.

3. The method set forth in claim 2, wherein said at least part of the cell wall is removed by irradiation with a laser beam or by irradiation with the laser beam and treatment with a hydrolysis enzyme in combination.

4. The method set forth in claim 1, wherein the small particle is a fine particle having a particle diameter of 0.01 Jtm to 10 µm.

5. The method set forth in claim 1, wherein the small particle is a liposome including the foreign matter.

6. The method set forth in claim 1, wherein the foreign matter is fixed by adding an aqueous solution containing at least the foreign matter and a curing agent into a water-in-oil type emulsion having a curable raw material in water, and forming a cured reaction product.

7. The method set forth in claim 6, wherein the curable raw material is sodium alginate, the curing agent is calcium chloride, and the cured reaction product is calcium alginate.

8. The method set forth in claim 1, wherein the laser is at least one laser selected from the group consisting of a YAG laser, an exima laser, an Ar ion laser, a nitrogen laser and a nitrogen-excited color laser.

9. The method set forth in claim 1, wherein the foreign matter is at least one material selected from the group consisting of a genetic material, a protein material, an organella, a physiologically active material and an indicating agent.

10. The method set forth in claim 9, wherein the genetic material is at least one selected from the group consisting of a DNA, a RNA, an oligonucleotide, a plasmid, a chromosome, an artificial chromosome, an organella DNA and a nucleic acid analogue.

11. A method for introducing a foreign matter into a cell, comprising the steps of:
   placing a small particle carrying a foreign matter at a part of a cell surface of a living cell, wherein the small particle is a particle that carries the foreign matter and releases the carried foreign matter after being introduced into the cells,
   boring a hole in a cell wall and/or a cell membrane by irradiating and treating said part of the cell surface with a laser beam, and
   introducing the foreign matter into the living cell.

12. A method for introducing a foreign matter into a cell, comprising the steps of:
   placing a small particle carrying a foreign matter at a part of a cell surface of a living cell, wherein the small particle adsorbs the foreign matter,
   boring a hole in a cell wall and/or a cell membrane by irradiating and treating said part of the cell surface with a laser beam, and
   introducing the foreign matter into the living cell.

* * * * *